(12) United States Patent
Schönborn et al.

(10) Patent No.: US 9,433,350 B2
(45) Date of Patent: Sep. 6, 2016

(54) IMAGING SYSTEM AND METHOD FOR THE FLUORESCENCE-OPTICAL VISUALIZATION OF AN OBJECT

(75) Inventors: Karl-Heinz Günter Schönborn, Berlin (DE); Andreas Bembenek, Hannover (DE); Jörn Ole Becker, Berlin (DE); Martin Bock, Berlin (DE); Andreas Lutz, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 1179 days.

(21) Appl. No.: 13/376,795

(22) PCT Filed: Jun. 8, 2010

(86) PCT No.: PCT/EP2010/057995
§ 371 (c)(1),
(2), (4) Date: Jul. 12, 2012

(87) PCT Pub. No.: WO2010/142672
PCT Pub. Date: Dec. 16, 2010

(65) Prior Publication Data
US 2012/0268573 A1 Oct. 25, 2012

(30) Foreign Application Priority Data
Jun. 10, 2009 (DE) .......................... 10 2009 024 943

(51) Int. Cl.
*H04N 15/00* (2006.01)
*A61B 5/00* (2006.01)
(Continued)

(52) U.S. Cl.
CPC ........... *A61B 5/0059* (2013.01); *A61B 1/00009* (2013.01); *A61B 1/00096* (2013.01);
(Continued)

(58) Field of Classification Search
USPC .......................................................... 348/49
See application file for complete search history.

(56) References Cited

U.S. PATENT DOCUMENTS 4,765,737 A * 8/1988 Harris et al. .................. 356/336
5,503,904 A 4/1996 Yoshinaga et al.
(Continued)

FOREIGN PATENT DOCUMENTS

DE 196 35 038 A1 3/1998
DE 199 54 710 C1 3/2001
(Continued)

OTHER PUBLICATIONS

International Search Report dated Nov. 5, 2010 as received in application No. PCT/EP2010/057995.
(Continued)

*Primary Examiner* — Leron Beck
(74) *Attorney, Agent, or Firm* — Maschoff Brennan

(57) ABSTRACT

An imaging system for the fluorescence-optical visualization of a two-dimensional or three-dimensional object is provided. The imaging system comprising an illumination unit, which is designed and provided for emitting optical radiation in a predetermined wavelength range in order to illuminate the object and excite a fluorescent substance contained in the object, and a capturing unit, which is designed and provided for capturing an optical signal from the region of the object and for splitting the optical signal into a fluorescence signal having a first wavelength range and a signal of visible light having a second wavelength range. The optical capturing unit has an optoelectronic converter having a plurality of partial regions and serving for converting the fluorescence signal into a first electronic data signal and the signal of visible light into a second electronic data signal.

20 Claims, 11 Drawing Sheets

(51) Int. Cl.

| | | |
|---|---|---|
| *A61B 1/05* | (2006.01) | |
| *A61B 5/1455* | (2006.01) | |
| *G01N 21/64* | (2006.01) | |
| *G02B 21/16* | (2006.01) | |
| *G02B 21/36* | (2006.01) | |
| *H04N 5/225* | (2006.01) | |
| *H04N 5/33* | (2006.01) | |
| *H04N 9/04* | (2006.01) | |
| *A61B 1/00* | (2006.01) | |
| *A61B 1/06* | (2006.01) | |
| *A61B 1/04* | (2006.01) | |
| *A61B 19/00* | (2006.01) | |

(52) U.S. Cl.
CPC .......... *A61B1/00186* (2013.01); *A61B 1/043* (2013.01); *A61B 1/051* (2013.01); *A61B 1/0638* (2013.01); *A61B 5/14556* (2013.01); *A61B 5/418* (2013.01); *G01N 21/6456* (2013.01); *G02B 21/16* (2013.01); *G02B 21/365* (2013.01); *H04N 5/2253* (2013.01); *H04N 5/332* (2013.01); *H04N 9/045* (2013.01); *A61B 1/0005* (2013.01); *A61B 1/00048* (2013.01); *A61B 1/00172* (2013.01); *A61B 1/041* (2013.01); *A61B 2019/5231* (2013.01); *A61B 2019/5293* (2013.01); *H04N 2005/2255* (2013.01); *H04N 2209/048* (2013.01)

(56) References Cited

U.S. PATENT DOCUMENTS

| | | | |
|---|---|---|---|
| 5,901,816 A | 5/1999 | Camilleri | |
| 6,148,227 A | 11/2000 | Wagnieres et al. | |
| 6,223,069 B1 | 4/2001 | Pfeiffer et al. | |
| 6,293,911 B1 | 9/2001 | Imaizumi et al. | |
| 6,379,010 B1 * | 4/2002 | Suzuki et al. | 353/31 |
| 6,473,176 B2 | 10/2002 | Basiji et al. | |
| 6,491,715 B1 | 12/2002 | Abels et al. | |
| 6,631,286 B2 | 10/2003 | Pfeiffer et al. | |
| 6,821,245 B2 | 11/2004 | Cline et al. | |
| 6,826,424 B1 | 11/2004 | Zeng et al. | |
| 6,853,857 B2 | 2/2005 | Pfeiffer et al. | |
| 6,897,953 B2 | 5/2005 | Watanabe et al. | |
| 7,008,374 B2 * | 3/2006 | Hakamata | 600/109 |
| 7,307,774 B1 | 12/2007 | Schnitzer et al. | |
| 7,822,558 B2 * | 10/2010 | Kimura et al. | 702/23 |
| 7,884,337 B2 | 2/2011 | Hasegawa et al. | |
| 8,153,418 B2 * | 4/2012 | Kawashima | 435/288.7 |
| 8,606,350 B2 * | 12/2013 | Ishihara | 600/476 |
| 8,614,099 B2 * | 12/2013 | Nakada et al. | 436/172 |
| 8,626,271 B2 * | 1/2014 | Dunki-Jacobs et al. | 600/476 |
| 2002/0186813 A1 * | 12/2002 | Tamura et al. | 378/98.8 |
| 2003/0047683 A1 | 3/2003 | Kaushal | |
| 2004/0142485 A1 | 7/2004 | Flower et al. | |
| 2004/0186351 A1 * | 9/2004 | Imaizumi et al. | 600/160 |
| 2005/0157923 A1 | 7/2005 | Takahashi | |
| 2005/0221387 A1 | 10/2005 | Jibu | |
| 2005/0267340 A1 | 12/2005 | Ishihara et al. | |
| 2006/0025692 A1 | 2/2006 | Ishihara | |
| 2006/0089554 A1 | 4/2006 | Ishihara et al. | |
| 2006/0108509 A1 | 5/2006 | Frangioni et al. | |
| 2006/0239921 A1 | 10/2006 | Mangat et al. | |
| 2007/0015963 A1 | 1/2007 | Fengler et al. | |
| 2007/0161907 A1 | 7/2007 | Goldman et al. | |
| 2007/0263210 A1 | 11/2007 | Taguchi et al. | |
| 2007/0276230 A1 | 11/2007 | Miwa et al. | |
| 2008/0045841 A1 | 2/2008 | Wood et al. | |
| 2008/0097198 A1 | 4/2008 | Miwa et al. | |
| 2008/0161744 A1 | 7/2008 | Golijanin et al. | |
| 2008/0164413 A1 | 7/2008 | Shibayama | |
| 2008/0177140 A1 | 7/2008 | Cline et al. | |
| 2008/0228037 A1 | 9/2008 | Cline et al. | |
| 2009/0076380 A1 | 3/2009 | Thierman | |
| 2009/0203994 A1 | 8/2009 | Mangat et al. | |
| 2010/0222673 A1 | 9/2010 | Mangat et al. | |
| 2010/0287624 A1 * | 11/2010 | Lindqvist | 726/34 |

FOREIGN PATENT DOCUMENTS

| | | |
|---|---|---|
| DE | 100 59 070 C1 | 2/2002 |
| DE | 603 16 123 T2 | 5/2008 |
| DE | 10 2005 019 143 A1 | 6/2011 |
| EP | 1 688 083 A1 | 8/2006 |
| EP | 1 731 087 A2 | 12/2006 |
| EP | 1 254 630 B1 | 2/2007 |
| EP | 1 788 379 A1 | 5/2007 |
| EP | 1 291 643 B1 | 8/2007 |
| EP | 1 816 454 A1 | 8/2007 |
| EP | 2 017 591 A1 | 1/2009 |
| JP | 2002-219129 A | 8/2002 |
| KR | 1020050058431 A | 6/2005 |
| WO | 03/077741 A1 | 9/2003 |
| WO | 2005/034747 A1 | 4/2005 |
| WO | 2006/116634 A2 | 11/2006 |
| WO | 2007/016790 A1 | 2/2007 |
| WO | 2007/106624 A2 | 9/2007 |
| WO | 2008/031038 A2 | 3/2008 |
| WO | 2008/089545 A1 | 7/2008 |
| WO | 2009052466 A1 | 4/2009 |

OTHER PUBLICATIONS

EP Office Action dated Mar. 20, 2013 as received in Application No. 10 734 055.6.

European Search Report dated Jul. 1, 2015 as received in Application No. 15167414.0.

EP Office Action dated Apr. 1, 2016 as received in U.S. Appl. No. 15/167,414.

* cited by examiner

IMAGING SYSTEM AND METHOD FOR THE FLUORESCENCE-OPTICAL VISUALIZATION OF AN OBJECT

CROSS-REFERENCE TO A RELATED APPLICATION

This application is a National Phase Patent Application of International Patent Application Number PCT/EP2010/057995, filed on Jun. 8, 2010, which claims priority of German Patent Application Number 10 2009 024 943.5, filed on Jun. 10, 2009.

BACKGROUND

The invention relates to an imaging system for the fluorescence-optical visualization of a two-dimensional or three-dimensional object and to a method for the fluorescence-optical visualization of a two-dimensional or three-dimensional object.

Such an imaging system for the fluorescence-optical visualization of a two-dimensional or three-dimensional object, in particular of the body of a patient and the organs and/or tissue regions thereof, has an illumination unit and a capturing unit, which firstly illuminate the object, i.e. irradiate it with an optical radiation of visible and/or infrared light, and secondly capture an optical signal generated in or at the object on account of the irradiation. For this purpose, the illumination unit is designed for emitting optical radiation in a predetermined wavelength range in order to illuminate the object and excite a fluorescent substance contained in the object, while the capturing unit is designed and provided for capturing an optical signal from the region of the object and for splitting the optical signal into a fluorescence signal having a first wavelength range and a signal of visible light having a second wavelength range.

The fluorescence signal arises in a human body for example as a result of the excitation of a suitable contrast agent, for example in the form of a dye such as indocyanine green (ICG), which corresponds to a fluorescent dye that is already used conventionally in medicine as an indicator substance (e.g. for photometric liver function diagnosis and fluorescence angiography) in the case of heart, circulatory, liver and eye diseases. For this purpose ICG is administered for example intravenously or else for diffusion on the skin and is naturally eliminated from the body with a half-life of approximately 3-4 minutes depending on liver performance. ICG can be present as a sodium salt in powder form and can be dissolved in various solvents. The absorption and fluorescence spectrum of ICG is in the near infrared range. The maximum of the fluorescence spectrum is different depending on the solvent: it is at a wavelength of approximately 830 nm in blood, and at approximately 820 nm in water (given an excitation wavelength of e.g. 765 nm).

In the case of an imaging system known from US2006/0108509 A1 visible light together with an excitation radiation in the infrared range is radiated onto an object, and an optical signal is captured from the region of the object. By means of beam splitters in the form of a mirror arrangement, the optical signal is then split into a first signal, corresponding to a fluorescence signal, in the infrared range and a second signal in the range of visible light. The signals are subsequently converted into electronic data signals by a plurality of electronic converters, processed further in a processing unit and displayed on a monitor.

In the case of an imaging system known from U.S. Pat. No. 6,293,911 B1 in a similar manner, an object is excited and an optical signal is captured from the region of the object. The optical signal is split into a signal of visible light and a fluorescence signal by means of a mirror arrangement, the signal of visible light subsequently being decomposed into a red, a green and a blue component (the so-called RGB colors) using a dichroic prism and processed further, as is also known from color video cameras, for example.

Both the arrangement in US2006/0108509 A1 and the system in U.S. Pat. No. 6,293,911 B1 use separate mirrors in order to separate fluorescence signals from signals of visible light. The resultant arrangements require a certain structural space for the provision of the mirrors and the propagation of light between the mirrors. Moreover, an extension of the channels of the arrangement for example for splitting and processing further signals is not readily possible.

SUMMARY

The present invention addresses the problem of an imaging system and a method for fluorescence-optical visualization of an object in which the capturing unit can be constructed compactly and it is possible to extend the number of channels for processing different signals in a simple manner.

According to an exemplary embodiment of the invention the optical capturing unit has an optoelectronic converter having a plurality of partial regions and servicing for converting the fluorescence signal into a first electronic data signal and the signal of visible light into a second electronic data signal.

In an imaging system as claimed, a single optoelectronic converter having a plurality of partial regions for converting the generated signals is used instead of a plurality of separate optoelectronic converters. In this case, the excited optical signal can be split for example in a multichannel dichroic prism, but also by means of a suitable mirror arrangement that splits the optical signal in a desired manner among the above-mentioned partial regions. The split signals are then fed to the optoelectronic converter, converted there into electronic data signals and forwarded, for example to a control and processing unit for further processing.

By virtue of using only one optoelectronic converter having a plurality of partial regions, the construction is simplified considerably. In particular, it is not necessary for a plurality of optoelectronic converters to be provided in parallel and interconnected with leads. Moreover, the signal read-out process can also be simplified since signals are only generated by one optoelectronic converter and correspondingly processed further.

By way of example, of the partial regions of the optoelectronic converter a first partial region converts the fluorescence signal into a first electronic data signal and a second partial region converts the signal of visible light into a second electronic data signal. Therefore, spatially separate regions are provided on the optoelectronic converter, to which the different signals are fed and which convert the signals spatially separately. Separation of the fluorescence signal from the signal of visible light and conversion at partial regions that are spatially separate from one another are necessary in order that the fluorescence signal, which is very much weaker in terms of its intensity, can be received in a manner undisturbed by the signal of visible light and can be converted with sufficient sensitivity.

By using a dichroic prism connected to the optoelectronic converter and serving for splitting the captured optical signal into the fluorescence signal and the signal of visible light, an arrangement is provided which can dispense with further beam-splitting mirrors for splitting the optical signal. The fluorescence signal and the signal of visible light are separated from one another by means of a dichroic prism. In this way, a compact construction is obtained which can manage with a single prism for beam splitting and additionally ensures short propagation paths between signal splitting and signal detection. As a result, the system is firstly comparatively simple to construct and, moreover, less sensitive to disturbances during operation.

Furthermore, by using a dichroic three-channel or four-channel prism or a prism having even more than four channels, it is possible to scale the number of channels in the system in a simple manner, such that the captured optical signal can be split into a plurality of different components which can subsequently be processed separately.

In this context a dichroic prism should be understood to mean an optical prism which splits a light beam into at least two beams having different spectra, i.e. in different wavelength ranges. It is usually produced from glass, specific surfaces being provided with dichroic mirrors that reflect or transmit light depending on the wavelength thereof.

In one exemplary embodiment of a dichroic prism, the optical signal in the form of a light beam enters into a first partial prism and impinges on a first dichroic filter, which reflects a first component of the optical signal having a first wavelength range and transmits the rest of the light, for example light having longer wavelengths. This light enters into a second partial prism and is split by a second dichroic filter, which reflects a second component of the light and transmits a third component. The angles of the individual partial prisms are chosen such that the first and second components are deflected by means of total reflection in the respective partial prisms.

The first wavelength range and the second wavelength range of the fluorescence signal and of the signal of visible light, respectively, differ from one another. The first wavelength range, corresponding to the wavelength range of the fluorescence signal, can contain, for example, wavelengths of greater than 800 nm and thus lies in the infrared range. By contrast, the second wavelength range of the signal of visible light can contain wavelengths of less than 700 nm and thus lies in the range of the visible wavelengths.

The optoelectronic converter connected to the dichroic prism, for example designed as CMOS or CCD components, is advantageously arranged directly on the dichroic prism and connected to the dichroic prism in such a way that the respective signals impinge on the converter, are converted there into electronic signals and forwarded for electronic further processing.

For the detection of the fluorescence signal, a long-pass filter can additionally be arranged upstream of the optoelectronic converter (e.g. in the form of a CCD chip), which filter only transmits wavelengths greater than the limiting wavelength for the fluorescence signal (e.g. 800 nm).

The optoelectronic converter can be designed for example as a black-and-white converter or as a color converter. As a black-and-white converter, for example, a so-called "B/W NIR enhanced" converter can be designed in particular for the reception of optical signals in the (near) infrared range (NIR: Near Infrared). By way of example, a photosensor designated as a Bayer sensor or Bayer pattern can be used as a color converter, said photosensor being equipped with a color filter consisting e.g. of 50% green and in each case 25% red and blue (taking account of the fact that the human eye reacts more sensitively to green than to other colors). In order to obtain color information, in this case in a manner known per se, a color filter in one of the three primary colors red, green or blue is applied upstream of each individual photocell of the sensor. Each color point (pixel) accordingly only supplies information for a single color component at this location such that, for a complete image having the same dimensions, the respectively adjacent pixels of the same color have to be used for color interpolation.

It is also conceivable for different regions of the optoelectronic converter to be designed differently, for example for a first partial region for converting the fluorescence signal to be designed as a black-and-white converter, and a second partial region for converting the signal of visible light to be designed as a color converter.

In one specific configuration, the optoelectronic converter can have a number of pixel elements each consisting of four individual pixels, three individual pixels being designed for converting the signal of visible light and one individual pixel being designed for converting the fluorescence signal. Consequently, the optoelectronic converter has a number of regularly arranged pixel elements, each consisting of four individual pixels. Of these four individual pixels, by way of example, a first can be sensitive to red light, a second to green light and a third to blue light (that is to say that three individual pixels which are sensitive in the range of visible light exist per pixel element) and a fourth individual pixel can be designed for receiving infrared light.

This results in pixel elements which consist of groups of (in each case four) individual pixels and which can in each case inherently detect both visible light and infrared light. This makes it possible to produce the optoelectronic converter as a uniform chip which is irradiated with different signals in different regions (for example with the fluorescence signal in a first region and with the signal of visible light in a second region) and then converts the signals in a suitable manner in each case.

In addition, it may be provided that the three individual pixels for converting the signal of visible light are also designed for converting the fluorescence signal. All the individual pixels can thus receive the fluorescence signal in the range of the infrared light, such that the fluorescence signal (of weak intensity) is detected by all the individual pixels. The color components of the (stronger) signal of visible light (red, green and blue) by contrast are in each case converted only by one individual pixel.

In the case where the dichroic prism is designed as a three-channel prism provision may be made for additionally splitting the captured optical signal into a fluorescence excitation signal having a third wavelength range which differs from the first wavelength range and the second wavelength range and lies in a wavelength range of between 700 nm and 800 nm, that is to say between the signal of visible light (having wavelengths of less than 700 nm) and the fluorescence signal (having wavelengths of greater than 800 nm). This wavelength range preferably corresponds to the range of the radiation emitted by the illumination unit for exciting the fluorescence of the object or of a fluorescent substance contained in the object.

It is possible to connect the third channel of the dichroic prism to an absorber element in the form of a black glass for example, which absorbs the fluorescence excitation signal. In this way, an imaging system is provided which utilizes only the component of the captured optical signal in the visible wavelength range of less than 700 nm and in the infrared range of greater than 800 nm for obtaining information, but suppresses the range therebetween. If the optical excitation radiation of the illumination limit for illuminating the object and exciting a fluorescent substance contained in the object lies precisely in this range, that is to say has wavelengths of between 700 nm and 800 nm, it is thereby possible to minimize the stray light within the capturing unit and to improve the contrast of the received signals.

Alternatively however, it is also possible to connect the dichroic prism to a further optoelectronic converter (or to provide a further partial region of a single optoelectronic converter), which converts the fluorescence excitation signal into a third electronic data signal. This affords the possibility of utilizing the signal in the wavelength range of between 700 nm and 800 nm and of obtaining additional information therefrom. By way of example, from the third electronic data signal obtained from the fluorescence excitation signal, it is possible to obtain further image information about the object considered, it is possible to obtain information about the signal-to-noise ratio or it is possible to improve the meaningfulness of image information in a targeted manner. For example, in tissue regions of high absorption, non-fluorescent ("quenched") absorption mechanisms can have an effect, which mechanisms cannot be detected in a fluorescence image obtained from the fluorescence signal, but can indeed be detected in an absorption image obtained from the fluorescence excitation signal. In addition, the fluorescence image and the absorption image are approximately complementary in terms of their intensity. Subtraction or formation of the ratio of the corresponding images can accordingly serve to increase the contrast. Furthermore, it is possible to place the absorption image onto a significant absorption line (corresponding e.g. to hemoglobin) and to evaluate it separately.

The further optoelectronic converter, like the converter that captures the fluorescence signal, for example, is designed as a black-and-white converter in the form of a "B/W NIR enhanced" CCD chip.

In one embodiment, the further optoelectronic converter for detecting the fluorescence excitation signal resulting from the excitation radiation, can interact with a beam attenuation filter in order to attenuate the high-intensity fluorescence excitation signal in a suitable manner such that the latter can be processed by the electronic converter. The attenuation filter can consist for example of a filter glass, e.g. a gray glass filter.

Instead of a further optoelectronic converter it can also be provided that the optoelectronic converter having a plurality of partial regions has a third partial region, which converts the fluorescence excitation signal into a third electronic data signal. The optoelectronic converter thus has three partial regions, of which a first detects and converts the fluorescence signal, a second detects and converts the signal of visible light, and a third detects and converts the fluorescence excitation signal.

As an alternative thereto, it is also possible for a partial region of the optoelectronic converter having a plurality of partial regions to capture and convert both the signal of visible light and the fluorescence excitation signal. The optoelectronic converter therefore manages with two partial regions, of which a first converts the fluorescence signal and a second converts the signal of visible light and the fluorescence excitation signal.

The imaging system provided makes it possible, in particular, for a physician to visualize non-visible vessels, organs or organelles (e.g. for representing the lymphatic system with the lymph nodes incorporated therein) intra-operatively. In this case, the imaging system can be used firstly open-surgically for the fluorescence-optical visualization by illumination and capture from outside and secondly for example endoscopically or colposcopically for the fluorescence-optical visualization by illumination and capture inside a patient. For this purpose, the capturing unit can be connected to a lens for capturing the optical signal outside the object and/or to a capturing device for capturing the optical signal from the interior of the object. The capturing device for capturing the optical signal from the interior of the object can be, for example, an endoscope, a colposcope, a camera that can be inserted or introduced into the object invasively or non-invasively, for example in the form of a camera to be used intra-orally or in the form of a so-called "pill-cam" to be swallowed by a patient in the form of a pill, wherein other configurations of a capturing device that can be introduced into a patient are also considerable (the illumination unit can be realized in this case e.g. in the pill as a light source that has a chemoluminescent action and can be triggered by gastric acid, for example). The capturing unit can optionally be connected to the lens for capturing an optical signal outside the object and/or to the, for example, endoscopic capturing device for capturing the optical signal from the interior of the object, the capturing device being detachable in a simple manner. In this way, a diversely useable imaging system is provided which can optionally be used open-surgically or endoscopically and for this purpose merely requires the exchange of individual ancillary components.

Besides the capturing unit the imaging system has an illumination unit, which serves for illuminating and exciting the object to be examined and for this purpose emits optical radiation in a predetermined wavelength range. For this purpose the illumination unit can be equipped with two light sources, of which a first light source generates a fluorescence excitation radiation and a second light source generates radiation in the range of visible light (white light). The fluorescence excitation radiation generated by the first light source can be, for example, in a wavelength range of between 700 nm and 800 nm, while the radiation of visible light preferably has wavelengths of less than 700 nm. The light sources can be realized, for example, by lasers or light-emitting diodes (LEDs) which are in each case adapted for generating optical radiation in the desired wavelength range with the required intensity and characteristic.

The radiation generated by the two light sources of the illumination unit is advantageously coupled into an optical waveguide by an optical coupling element for coupling the fluorescence excitation radiation and the radiation in the range of visible light. The optical coupling element can additionally have dichroic filter layers and couples the fluorescence excitation radiation and the radiation in the range of visible light, for example, physically or by fiber-optic combination.

By means of the optical waveguide, the coupled radiation is guided toward the object for the purpose of illumination, wherein the optical waveguide can be connected to an element for adapting the emission characteristic of the optical radiation for illuminating the object from outside or for illuminating regions within the object. By way of example, the optical waveguide, for adapting the emission characteristic, can be connected to a diffuser and/or an endoscope, in order to illuminate the object from the outside or from the inside and to guide the optical radiation in a targeted manner to the location at which the object is intended to be illuminated and excited for the fluorescence-optical visualization. In other words, by means of the optical waveguide and, if appropriate, an endoscope or the like, the optical radiation is guided in a targeted manner into the region from which the capturing unit then receives the desired optical signals. In this case, illumination unit and capturing unit can use the same endoscope firstly for illumination and secondly for capture, in which endoscope firstly a light-guiding channel for the optical (illumination) radiation and a light-guiding channel for the captured optical signal are arranged.

It may be conceivable and advantageous in this context to arrange the dichroic prism for splitting the captured optical signal into the fluorescence signal and the signal of visible light directly in the tip of an endoscope, that is to say at that end of the endoscope which is to be inserted into the object, in order to capture the optical signal directly where it arises. In this way, it is possible to dispense with a light-guiding channel in the endoscope for guiding the captured optical signal toward the dichroic prism, such that signal losses as a result of transmission are avoided or at least minimized to the greatest possible extent. The optical signal is thus already acquired at the location where it arises, and is converted directly into electronic data signals at the dichroic prism after signal splitting, said data signals then being communicated via the endoscope to a control and processing unit for further image processing and analysis.

A control and processing unit is provided, inter alia, for controlling the illumination unit and/or the capturing unit and thus the functioning of the imaging system. In this case, the control and processing unit firstly prescribes parameters for the operation of the illumination unit and the capturing unit and regulates the interaction thereof, and secondly it performs the processing of the signals captured by means of the capturing unit and converted into electronic data signals.

For the purpose of image processing, the control and processing unit can be designed to generate from the acquired signals a real image obtained from the signal of visible light, a fluorescence image obtained from the fluorescence signal and/or an infrared absorption image obtained from a fluorescence excitation signal which can be output in a superimposed manner or alongside one another and displayed to a physician for assessment. If the images obtained are intended to be represented in superimposed fashion, then the images assigned to one another are algorithmically fused with one another in a form pretreated digitally or in analog fashion. The fusion is effected, for example, in such a way that regions in which a signal was detected on the fluorescence image obtained on the fluorescence signal are marked on the real image with false colors. As one possibility for a pretreatment algorithm of the fluorescence image, a threshold value is defined, upon the exceeding of which a signal is transmitted to the real image. The region with fluorescence intensities above the threshold is marked in the real image with a selectable false color in real time. In this case, by way of example, in the sense of a yes-no decision, only the fact of the fluorescence radiation or a fluorescence signal proportional to the signal intensity can be displayed. Other scalings, such as intensity representations of the fluorescence signal that are logarithmic or limited by a maximum value, are also conceivable.

In a further configuration, the imaging system can have a two-axis scanner for projecting a generated fluorescence image onto the object. The two-axis scanner can be designed, for example, to direct a light beam of a light source for generating a fluorescence image on the object periodically over the object, in order in this way to generate an image on the object which corresponds to the fluorescence image generated from the fluorescence signal. In this way, such regions in which a fluorescence signal is present can be displayed directly in false colors for example on the object. It is thus possible to display to a physician during an operation in real time a fluorescence image directly where it originates, such that an additional monitor for displaying the fluorescence image could even be obviated.

Additionally or alternatively, the two-axis scanner can be designed to direct optical radiation of a light source for excitation of a fluorescence signal onto the object and/or to direct excited optical signals from the object toward a detector. By means of the two-axis scanner, a pixel-by-pixel excitation and/or capture can thus be effected, in which case a laser, for example, can be used as a light source for the purpose of excitation.

Such a projection device can advantageously be combined with the imaging system described above, but can in principle also be operated independently in interaction with any other imaging systems.

Such an imaging system for the fluorescence-optical visualization of a two-dimensional or three-dimensional object can comprise, for example, in a general manner:

an illumination unit, which is designed and provided for emitting optical radiation in a predetermined wavelength range in order to illuminate the object and excite a fluorescent substance contained in the object, a capturing unit, which is designed and provided for capturing a fluorescence signal from the region of the object, wherein provision is made of a two-axis scanner for projecting a fluorescence image generated from the fluorescence signal onto the object.

The imaging system can direct a light beam of a light source for generating a fluorescence image on the object periodically over the object, wherein the excitation of the fluorescence signal and the imaging of the fluorescence image obtained from the fluorescence signal can preferably be effected alternately, that is to say in a manner of time division multiplexing.

In this case, it may also be provided that the two-axis scanner is additionally designed for the excitation and capture of the fluorescence signal and thus also realizes the illumination unit and the capturing unit. By means of the two-axis scanner, alternately a signal is excited and received in a first time window and a fluorescence image generated therefrom is imaged on the object—that is to say precisely where it has been generated—in a second time window.

Alternatively, steps (a) fluorescence excitation, (b) fluorescence radiation measurement and (c) projection of a visible display projection beam increasing monotonically with the measured fluorescence signal (fluorescence image projection) can be performed in direct temporal succession, virtually simultaneously. Capture and imaging are thus advantageously achieved with minimal temporal and technical expenditure.

Such an arrangement is suitable, in particular for open-surgical applications.

The problem is furthermore solved by means of a method for the fluorescence-optical visualization of a two-dimensional or three-dimensional object, in which an optical radiation is emitted in a predetermined wavelength range in order to illuminate the object and excite a fluorescent substance contained in the object, and an optical signal is captured from the region of the object and the optical signal is split into a fluorescence signal having a first wavelength range and a signal of visible light having a second wavelength range.

In the method, it is provided that a dichroic prism splits the captured optical signal into the fluorescence signal and the signal of visible light and an optoelectronic converter connected to the dichroic prism and having a plurality of partial regions converts the fluorescence signal in a first electronic data signal by means of a first partial region and converts the signal of visible light into a second electronic data signal by means of a second partial region.

The same advantages as described above for the imaging system arise for the method according to the invention.

The described imaging system and the method can be used in a wide field particularly for medical purposes. By way of example, this includes finding specific significant organs, organelles or organ parts or pathologically altered tissue regions (lymph nodes, lymph vessels, veins, bile ducts, cavities, foci of inflammation or the like) in the human body with the aid of dyes introduced into the body and the imaging detection thereof by means of fluorescence-optical methods and observing substance transport phenomena in endogenous flow systems (veins, lymph vessels, skin perfusion and others) and/or qualitatively and quantitatively determining transport speeds and routes and accumulation areas and volumes of said flow systems.

The following medical purposes of use are specifically conceivable, although the enumeration should not in any way be understood as exhaustive:
- visualization of the lymphatic system with the aim of lymphography (minimally invasive),
- sentinel lymph node biopsy (e.g. for breast, malignant melanomas, lung, stomach, intestine, prostate gland, cervix, endometrium),
- visualization of the blood vessel system (perfusion measurement) with the aim of anastomosis monitoring,
- determining degree of severity in the case of burns (minimally invasive),
- determining a required amputation level (minimally invasive)
- quality check during reconstruction operations, plastic corrections or tissue grafts,
- assessment of "diabetic foot" syndrome (minimally invasive),
- decubitus monitoring (minimally invasive),
- representing so-called "bleeding points" in the context of endoscopic operations,
- differentiating between types of tissue (e.g. adenoma vs. tumor),
- obtaining information about the invasion depth of identified tumors (submucosal effect),
- visualization of bile ducts in the context of liver or gall bladder surgery with the aim of preserving important structures.
- visualization of degenerations for cancer check-up (so-called "screening") and the early identification of tumors (e.g. in connection with selective tumor markers) (minimally invasive).

"Minimally invasive" should be understood here to mean that the purposes of use indicated thus necessitate at least the use of a fluorescent contrast agent introduced into a body in order to obtain a fluorescence signal from the body.

In principle, the procedure here is such that a dye introduced into a patient's body either systemically (by injection) or topically (by application to the surface of the body and diffusion) (or the agglomerations—which form in the body after introduction—of said dye with endogenous substances) is excited to fluorescence by radiation emitted by the illumination unit, the resulting fluorescence signal is detected by means of the capturing unit and a fluorescence image generated therefrom is displayed in a manner that allows the physician to take diagnostic or therapeutic decisions.

BRIEF DESCRIPTION OF THE DRAWINGS

The concept on which the invention is based will be explained in greater detail below on the basis of the exemplary embodiments illustrated in the figures.

DETAILED DESCRIPTION

Figure 1:
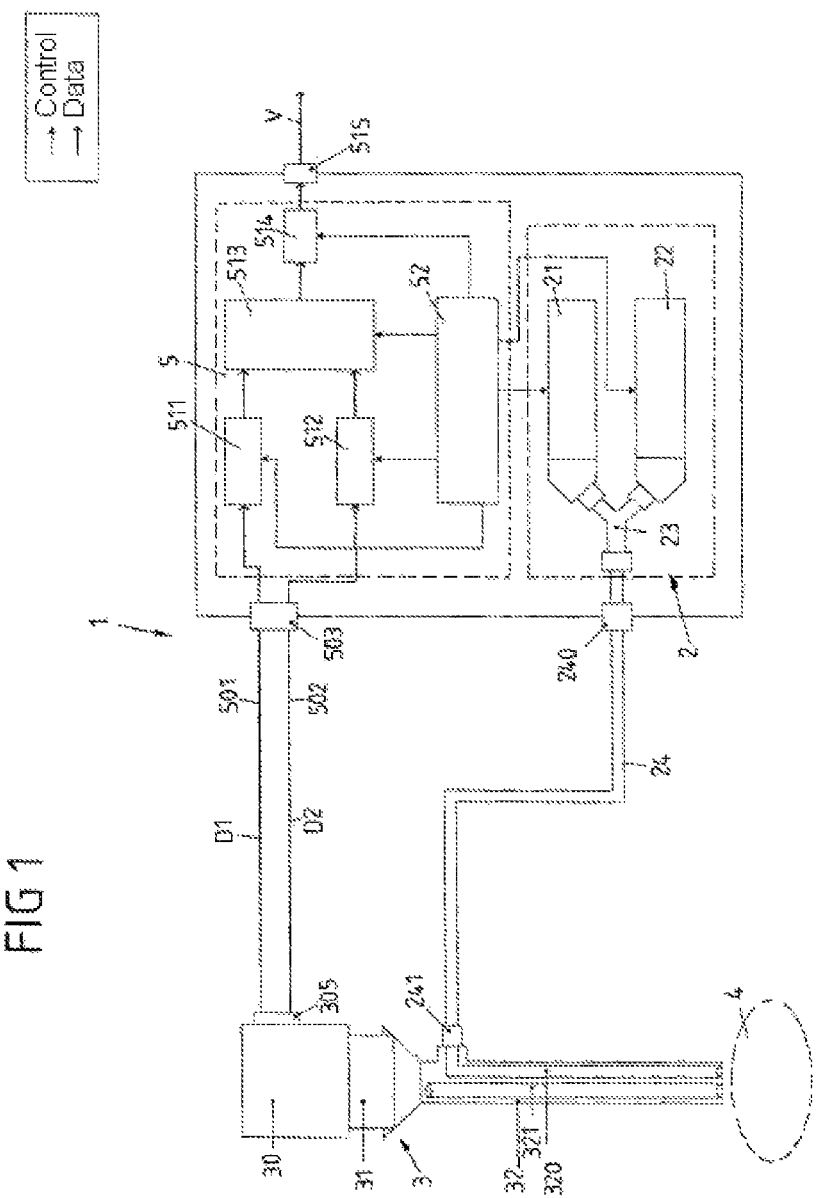
FIG. 1 shows a schematic view of a first embodiment of an imaging system comprising an illumination unit and a capturing unit, in which, by means of a dichroic prism, a captured optical signal is split into a fluorescence signal and a signal of visible light (2-channel variant).

FIG. 1 firstly shows in an overview illustration an embodiment of an imaging system 1 comprising an illumination unit 2 and a capturing unit 3. The imaging system 2 serves for the fluorescence-optical visualization of an object 4, for example of vessels, organs or organelles of a patient, and for this purpose generates an optical radiation by means of which the object 4 is irradiated and excited to emit fluorescence-optical signals.

The following procedure is basically adopted for the fluorescence-optical visualization. Firstly, a suitable fluorescent dye (for example indocyanine green (ICG)), is introduced into the object 4, for example a patient's body. This can be done systemically by injection or topically by application to the surface of the object and diffusion. Afterward, the introduced dye is excited to fluorescence by means of the illumination unit 2, and the resulting signals are detected by means of the capturing unit 3. The detected signals are processed further and displayed to a physician for assessment in a suitable manner, for example as a video signal in real time.

It should be emphasized at this juncture that the functioning of the imaging system is independent of the manner in which the fluorescence substance is introduced into the object 4. All that is essential is that a substance that can be excited to fluorescence is present in the object 4. In principle, this substance can also be present naturally in the object 4 without introduction from outside being necessary.

The illumination unit 2 has two light sources 21, 22, which, by means of lasers or light-emitting diodes (LEDs) generate firstly a fluorescence excitation radiation in a wavelength range of between 700 nm and 800 nm and secondly a radiation in the range of visible light having wavelengths of less than 700 nm. The radiation generated by the light sources 21, 22 is coupled by means of an optical coupling element 23, for example in the form of a physical or fiber-optic coupler, and fed into an optical waveguide 24, for example a flexible optical fiber, via a connection 240.

By means of the optical waveguide 240, optical radiation generated is guided toward an endoscope 32 connected to the capturing unit 3 and is connected to the endoscope 32 via a connection 241. The endoscope 32 has a light-guiding optical channel 320, in which the optical radiation of the illumination unit 2 is guided toward the object 4.

The endoscope 32 is designed for insertion into the object 4. By way of example, the endoscope 32 can be inserted invasively into a patient's body in order in this way to excite vessels or organs of the patient directly inside the patient. The endoscope 32 can be designed to be flexible at least in sections in a manner known per se and thus enables simple access into the interior of the object 4.

The endoscope 32 has a second channel 321, via which optical signals resulting from the optical excitation are captured in or at the object 4 and are guided to the capturing unit 3. For this purpose, the endoscope 32 is connected via a lens 31 having a quick-release fastener to a camera head 30 of the capturing unit 3, in which camera head the received optical signals are decomposed and converted.

Figure 2:
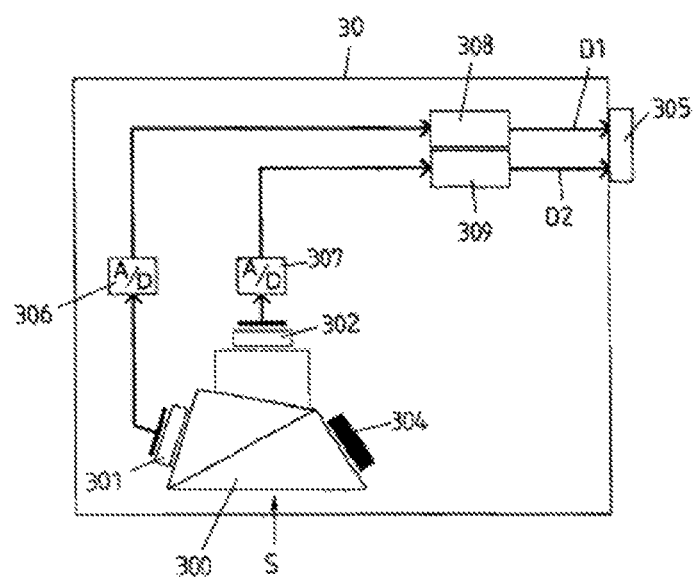
FIG. 2 shows a detail illustration of the capturing unit of the imaging system in accordance with FIG. 1.

A detail view of the camera head 30 is illustrated in FIG. 2. A dichroic prism 300 is arranged in the camera head 30, said prism being connected to two optoelectronic converters 301, 302 in the form of CCD chips or CMOS components and additionally being connected to an absorber element 304 for example in the form of a black glass. The dichroic prism 300 serves for the beam splitting of a received optical signal S impinging on the dichroic prism 300 and decomposes said signal, as will also be explained below with reference to FIG. 3, into signal components S1, S2, S3 corresponding to a fluorescence signal having wavelengths of greater than 800 nm, a signal of visible light having wavelengths of less than 700 nm, and a fluorescence excitation signal having wavelengths of between 700 nm and 800 nm. Of these signal components, only the fluorescence signal S1 and the signal of visible light S2 in the construction in accordance with FIG. 2 are detected by means of a respective optoelectronic converter 301, 302 and converted into electronic data signals D1, D2 by means of analog/digital converters 306, 307 and electronic drivers 308, 309. The fluorescence excitation signal S3, by contrast, is absorbed by means of the absorber element 304 and not fed for image processing.

As can be seen from FIG. 1, the camera head 30 is connected via a connection 305 to data cables 501, 502, via which the electronic data signals D1, D2 are conducted to a control and processing unit 5. For this purpose, the data cables 501, 502 are connected via a connection 503 to the control and processing unit 5, which is arranged in the same housing as the illumination unit 2.

The control and processing unit 5 serves firstly for the control of the illumination unit 2 and of the capturing unit 3 and secondly for the image processing of the received data signals D1 D2. For this purpose, the control and processing unit 5 has preprocessing units 511, 512 serving for the preprocessing of the electronic data signal D1 assigned to the fluorescence signal and of the electronic data signal D2 assigned to the signal of visible light. The preprocessed data signals are forwarded to an imaging processing unit 513, which generates algorithmically from the data signals D1, D2 a fluorescence image corresponding to the fluorescence signal and a real image assigned to the signal of visible light.

The image processing unit 513 can fuse the fluorescence image and the real image with one another, for example, that is to say superimpose them in such a way that such regions in which a fluorescence signal is present are displayed in false colors in a fused image on the real image. The image thus generated is forwarded to a final processing unit 514, which performs the so-called "framing" for the real-time representation of generated images and, via a connection 515, outputs a video output signal V for display on a monitor and for assessment for a physician.

The control and processing unit 5 has a control unit 52, which controls the individual units 511, 512, 513, 514 and at the same time also regulates the illumination unit 2, in particular with evaluation of the received data signals D1, D2.

Figure 3:
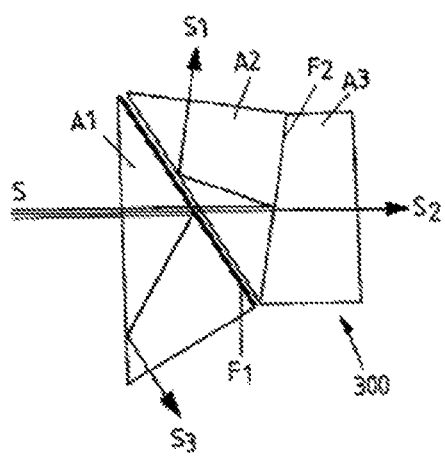
FIG. 3 shows a detail illustration of an embodiment of a dichroic prism.

A detail view of an embodiment of a dichroic prism 300 is illustrated in FIG. 3, in which case other embodiments can also be used, in principle. The dichroic prism 300 has three partial prisms A1, A2, A3, which are optically coupled to one another by means of dichroic filters F1, F2. The dichroic prism 300 serves for splitting an incident optical signal S into three partial signals corresponding to a fluorescence signal S1, a signal of visible light S2, and a fluorescence excitation signal S3. In this case, the incident optical signal S firstly impinges on that interface of the partial prism A1 which is provided with the dichroic filter F1, and is partly reflected and partly transmitted at said interface. The dichroic filter F1 is designed such that only the component of the optical signal S in the wavelength range of between 700 nm and 800 nm is reflected, but the remaining components are transmitted. The remaining components thus enter into the partial prism A2 and are partly reflected and partly transmitted at that interface of the partial prism A2 which is provided with the dichroic filter F2.

The dichroic filter F2 is constituted such that it transmits signals having wavelengths of less than 700 nm, but reflects signals having greater wavelengths. In this way, the fluorescence signal S1 is separated from the signal of visible light S2, the signal of visible light S2 entering into the partial prism A3 and passing through the latter, while the fluorescence signal S1, with total reflection within the partial prism A2 is once again reflected and emitted.

As is evident from FIG. 2, the fluorescence signal S1 and the signal of visible light S2 are detected and converted by a respective optoelectronic converter 301, 302 while the fluorescence excitation signal S3 is absorbed and not processed further in the case of the imaging system in accordance with FIG. 1.

The use of a dichroic prism 300 enables a compact construction of the imaging system 1 with its capturing unit 3. In particular, there is no need for separate mirrors for beam splitting. The beam splitting is effected completely by means of a uniform, compact dichroic prism.

The imaging system 1 can optionally be used endoscopically for the excitation of fluorescence-optical signals within an object 4, as illustrated in FIG. 1, or else open-surgically for the external illumination and capture of fluorescence-optical signals outside an object 4 without the use of an endoscope 32. The endoscope 32 can be released from the lens 31 for this purpose by means of a quick-release fastener. For open application, the optical waveguide 24 can then be connected, for example, to a diffuser for adapting the emission characteristic and for external illumination of the object 4.

A use of a diffuser for adapting the emission characteristic is also conceivable, in principle, in connection with an endoscope 32.

Figure 4:
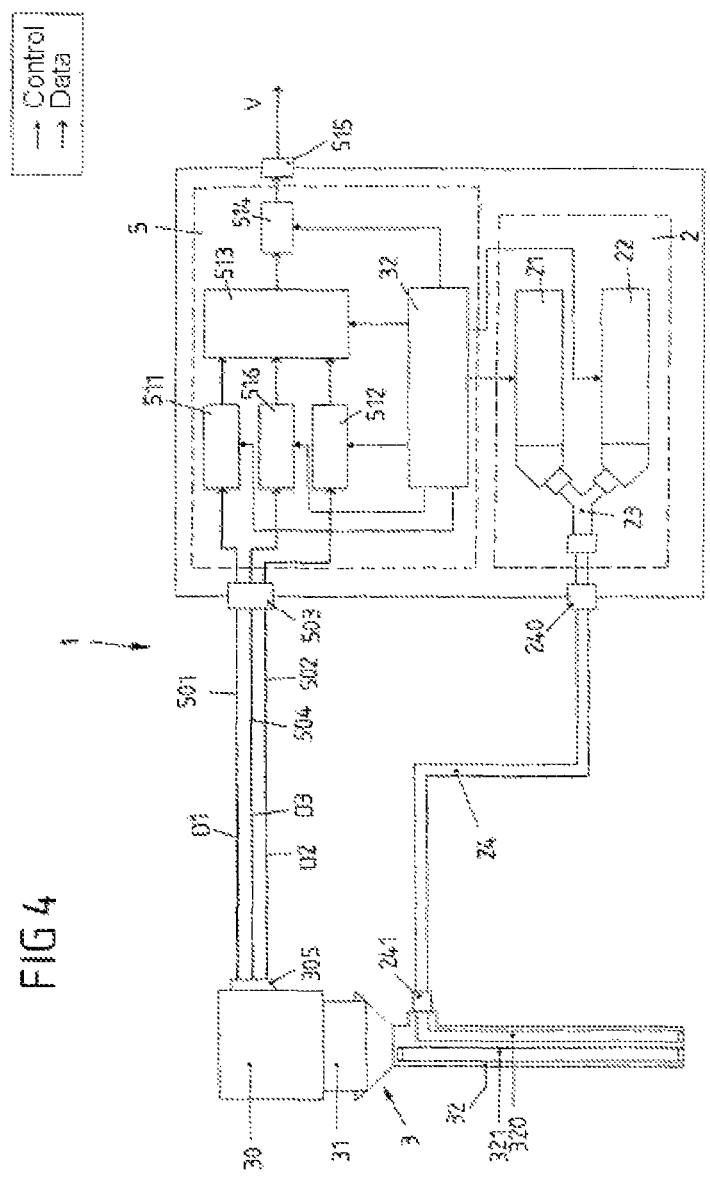
FIG. 4 shows a schematic view of a second embodiment of an imaging system comprising an illumination unit and a capturing unit, in which by means of a dichroic prism, a captured optical signal is split into a fluorescence signal, a signal of visible light and a fluorescence excitation signal (3-channel variant).
Figure 5:
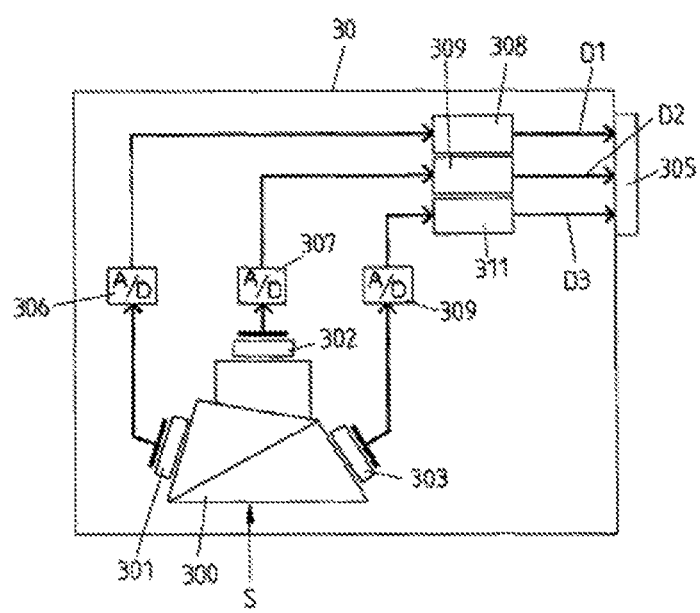
FIG. 5 shows a detail illustration of the capturing unit of the imaging system in accordance with FIG. 4.

A further embodiment of an imaging system 1 is illustrated in FIGS. 4 and 5. The construction basically corresponds to the construction of the imaging system 1 in accordance with FIGS. 1 to 3, identical structural parts also being designated by identical reference symbols insofar as is expedient.

In contrast to the imaging system 1 in accordance with FIGS. 1 to 3, in the imaging system 1 in accordance with FIGS. 4 and 5, the dichroic prism 300 of the capturing unit 3 is not connected to an absorber element 304 (cf. FIG. 2), but rather to a third optoelectronic converter 303 in the form of a CCD chip or CMOS component (see FIG. 5). The fluorescence excitation signal S3 separated in the dichroic prism 300 (see FIG. 3) is therefore not suppressed in the construction in accordance with FIGS. 4 and 5, but rather detected separately and converted into a third electronic data signal D3 by means of an analog/digital converter 309 and a driver 311, said third electronic data signal being fed via a connection 305, a data line 504 and the connection 503 to the control and processing unit 5. In a separate channel, the third electronic data signal D3 is preprocessed by means of an additional preprocessing unit 516 and fed to the image processing unit 513, which processes the additional signal in a suitable manner, derives information therefrom and, for example generates an infrared absorption image derived from the fluorescence excitation signal S3 and superimposes it on the real image and/or the fluorescence image.

The arrangement in accordance with FIGS. 4 and 5 thus provides an imaging system 1 comprising three channels and makes it possible to evaluate additional information to be derived from the fluorescence excitation signal. By way of example, from an infrared absorption image, it is possible to detect tissue regions in which a high degree of absorption occurs on account of non-fluorescent absorption mechanisms and which cannot be detected in the fluorescence image, but can indeed be detected in the infrared absorption image. Moreover, by subtraction or formation of the ratio of the infrared absorption image with the fluorescence image, it is possible to draw a conclusion about the signal-to-noise ratio. It is also possible to place the infrared absorption image onto a significant absorption line, corresponding for example to hemoglobin, and to evaluate this infrared absorption image separately.

Figure 6:
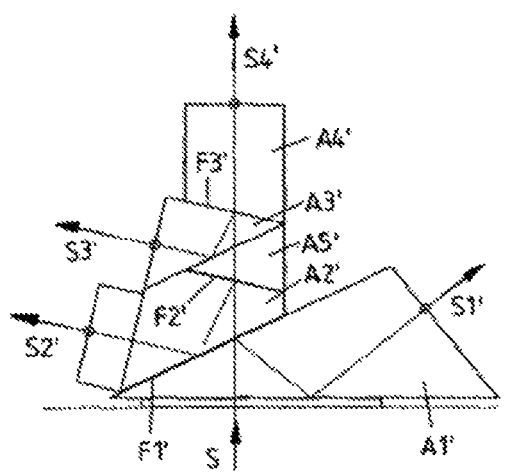
FIG. 6 shows an illustration of a 4-channel prism for splitting an optical signal into four signal components.

It is also conceivable, in principle, to use other dichroic prisms and to form a splitting of the optical signal S into further signal components using these prisms. FIG. 6 shows the four-channel prism, for example, which, using partial prisms A1', A2', A3', A4', A5', and dichroic filters F1', F2', F3', splits the optical signal S into partial signals S1', S2', S3', S4' which can be evaluated and processed separately from one another. In this case, the partial signals S1', S2', S3', S4' can be assigned to different wavelength ranges. It is conceivable, for example, by means of the four-channel prism, to split the optical signal S into three color signals (primary colors red, green, blue) and a fluorescence image.

It is also conceivable to split the optical signal S such that a real image, a fluorescence image, an infrared absorption image and a narrow band image (so-called "narrow band imaging"), are obtained.

By means of so-called "narrow band imaging", it is possible to improve for example the visibility of capillaries, veins and other fine tissue structures. For this purpose, discrete wavelengths are used in order to reduce absorption and reflection, firstly blue (415 nm) being used in order to represent the superficial capillaries and secondly green (540 nm) being used in order to represent deeper vessels. In combination this results in an image of the upper tissue layers with very high contrast.

In a first application of a four-channel prism, by way of example, the three primary colors red, green, blue are detected using a respective black-and-white converter while the fluorescence signal having wavelengths of greater than 800 nm is detected in the fourth channel.

In a second application of a four-channel prism, a color converter is used for the real image, the fluorescence image is supplied by a black-and-white "NIR-enhanced" converter, the infrared absorption image is likewise obtained by means of a black-and-white "NIR-enhanced converter" and a fourth converter operates in a "narrow band imaging" mode.

In a third application of a four-channel prism, a color sensor is used for the real image, a black-and-white "NIR-enhanced" converter is used for the fluorescence image, while a third converter supplies the blue band (415 nm) and a fourth sensor supplies the green band (540 nm) for so-called "narrow band imaging".

In principle, when using a four-channel prism too, it is possible to absorb one or a plurality of the signal components using one or a plurality of absorber elements, in order thereby to improve contrast and signal-to-noise ratio.

In a further-reaching configuration of an imaging system it is also conceivable to perform the excitation and capture of the optical signal S by means of time-division multiplexing in order in this way to achieve a temporal separation of the fluorescence signal S1 and of the signal of visible light S2 in addition to or instead of the beam splitting by means of the dichroic prism. For this purpose, the real image and/or the fluorescence image can be captured in a temporally alternating fashion by means of the same sensor. Real image and fluorescence are then separated by virtue of the fact that image-synchronously the two light sources 21, 22 for the radiation in the range of visible light and for the fluorescence excitation radiation are clocked synchronously with the corresponding image capture for the real image channel and the fluorescence image channel.

Two approaches are possible in this case:
1. alternately switching on and off the light sources 21, 22 for the fluorescence excitation radiation and the radiation of visible light;
2. clocking exclusively the fluorescence excitation radiation and calculating the fluorescence image as the difference between the image with and without fluorescence excitation.

For this purpose, it is possible, in principle to use a uniform color converter as a sensor. However, it is also conceivable to use a construction as in FIG. 1 or FIG. 4 and to perform a temporal separation in addition to the beam splitting by means of the dichroic prism 300.

When a uniform color converter is used, the light incident on the color converter can be filtered by a band-stop filter such that no excitation radiation is incident on the color converter (excitation radiation filter). In this way, it becomes possible to detect both a real image in the form of a color image and a fluorescence image by means of the sensor.

As indicated above, CCD chips or CMOS components can be used as optoelectronic converters 301, 302, 303. Particularly when CMOS sensors are used, it is possible to achieve effective suppression of extraneous light, that is to say suppression of such light and such radiation which does not originate from the illumination unit 2, but rather from external light sources in the surroundings, e.g. daylight.

In principle, such suppression of extraneous light is also possible using CCD chips.

Suppression of extraneous light is achieved by so-called "gating", for which there are basically two application possibilities:
1. suppression of disturbing light (ambient light); and
2. generation of the real image and of the fluorescence image by means of a CCD arrangement for the real image and the fluorescence image using time division multiplexing.

In the context of the first possibility, it is possible to drive an image sensor in the form of an optoelectronic converter (analogously to selection of exposure time in the case of a photographic camera) by controlling via an input at the sensor when the latter captures the signal. When using sensitive sensors (e.g. CMOS) it is thereby possible to reduce the exposure time of the sensor, as a result of which the influences of disturbing radiation are suppressed and external ambient light has no influence on a fluorescence image.

In the case of the second variant, it is possible to control capture synchronously with the light sources—likewise to be clocked—for the radiation of visible light and the fluorescence excitation radiation, as a result of which a real image and a fluorescence image are obtained alternately.

In order to increase the sensitivity of the optoelectronic converters for the detection of the infrared or near infrared signals, it is also possible to use so-called "binning", which involves aggregating adjacent sensor cells with simultaneous reduction of the spatial resolution. As a result, a plurality of pixels of the sensors are combined with one another by the signal values of adjacent cells being added and a higher signal value thereby being obtained for a location. The area of the detected signal location increases with the number of pixels, such that the spatial resolution decreases overall. One advantage of this method over pure signal amplification resides in the averaging of the background noise.

The fluorescence signal can additionally be optimized by the use of a suitable dye. By way of example, instead of the dye indocyanine green (ICG) it is possible to use a mixture of ICG and patent blue in order in this way to visualize possible contaminants as a result of the inherently invisible fluorescence dye. In this way, by way of example, contaminated swabs can be immediately replaced before they are used in an operation.

It is also conceivable to use combined LED light sources with the possibility of modulation, clocking and synchronization with the capturing unit 3.

It is additionally conceivable, when using a dichroic prism 300 in its three-channel form or four-channel form, to replace one optoelectronic converter by an illumination channel, such that the illuminating radiation is not fed to the object 4 via a diffuser or endoscopic light-guiding connection, but rather directly via the dichroic prism 300. For this purpose, an adapter can be present at the dichroic prism 300, said adapter enabling the connection of the optical waveguide 24 of the illumination unit 2.

Figure 7:
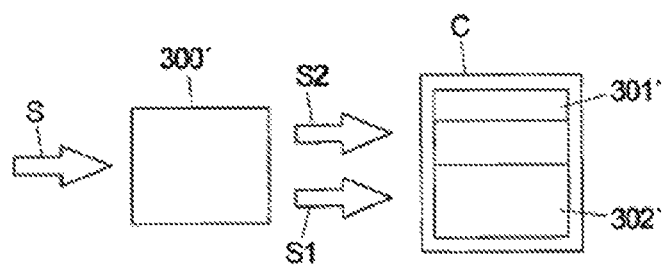
FIG. 7 shows a schematic view of an arrangement for splitting an optical signal into two signal components and detection by means of a single CCD chip.
Figure 8A:
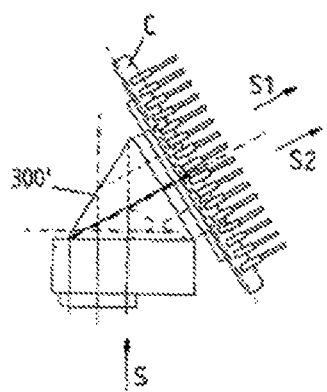
FIG. 8A shows a side view of an arrangement for detecting a split optical signal by means of a single CCD chip.
Figure 8B:
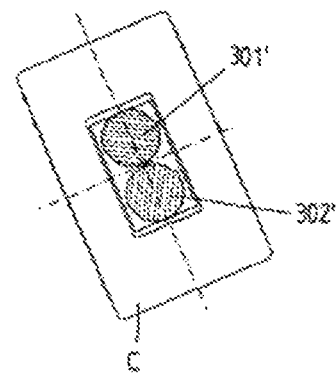
FIG. 8B shows a plan view of FIG. 8A.

FIGS. 7 and 8A, 8B schematically show an embodiment in which an optical signal S is split into signal components S1, S2, corresponding for example to a signal of visible light and a fluorescence signal, using a dichroic prism 300' and is detected by a single optoelectronic converter C, having two partial regions 301', 302' in the form of, for example, a color CCD chip (for example a 16:9 HD chip).

As illustrated schematically in FIG. 7 and for a specific configuration in FIGS. 8A, 8B, the optical signal S is split by means of a dichroic prism 300' and imaged onto different regions of the optoelectronic converter C, wherein some other dispersive element, e.g. a mirror arrangement or some other prism arrangement, can also be used, in principle for the purpose of beam splitting.

By using only one optoelectronic converter C, it is possible firstly to efficiently utilize the detector area of the optoelectronic converter C and secondly also to simplify the evaluation of the detected signals. In particular, the electronic processing chain for the downstream further processing of the image information is single-stranded owing to the single optoelectronic converter C used.

An advantageous processing method for the combination of the individual partial images additionally arises. This is because the pixels assigned to one another in the real image and in the fluorescence image lie in the same line of the optoelectronic converter and are merely offset by a specific number of pixels with respect to one another. In the read-out process following the detection of an image, using a so-called FPGA or DSP, for example, the image information can be processed in parallel in a pixel-conforming manner by storing the half-line output first and by outputting the line halves in an offset fashion, such that the image processing can proceed with an extremely short time delay. This is advantageous particularly during real-time capturing processes that are intended to enable a physician to track instrument movements made by said physician.

If appropriate, it is also possible electronically to perform an offset correction directly downstream of the optoelectronic converter C or in a downstream control and processing unit, by means of which an offset of the pixel locations is compensated for. The background here is that, during a read-out of half-lines, owing to tolerances, the locations assigned to the pixels of the half-line do not correspond exactly with respect to the imaged object in the image, with the result that an offset correction is necessary (a specific pixel of the half-line assigned to the fluorescence signal, owing to tolerances, possibly does not correspond to the same object detail as a corresponding pixel of the half-line assigned to the signal of visible light). In order to be able to carry out pixel-conforming, parallel processing of the half-lines an offset correction may therefore be necessary which can advantageously be performed by means of a simple operation in the manner of a shift register in an electronic element connected directly downstream of the image sensor.

FIGS. 8A and 8B show, in a side view (FIG. 8A) and a plan view of the optoelectronic converter C (FIG. 8B) a specific construction in which an optoelectronic converter C is disposed downstream of a dichroic prism 300' and in which the dichroic prism 300' images the optical signal S onto the partial regions 301', 302' of the optoelectronic converter C for example in the form of a CCD chip.

In the case of the arrangement in accordance with FIG. 8A the optical radiation S enters into the dichroic prism 300' from below and is partly reflected and partly transmitted at a separating surface of the dichroic prism 300' and is thus separated into a component corresponding to the signal of visible light S2 and a component corresponding to the fluorescence signal S1. This is done by means of a dichroic coating of the separating surface of the partial prisms of the dichroic prism 300'.

It is additionally possible to use blocking filters which are applied on the entrance surface of the dichroic prism 300' or are introduced into the equilateral dichroic prism 300'.

In the case of the solution illustrated in FIGS. 8A and 8B, one of the two partial images is mirrored, that is to say laterally reversed. By embodying a half-line memory as an LIFO memory, this can be elegantly corrected (in the case of an alternative prism arrangement without a mirror effect, a FIFO memory would accordingly have to be used).

If a color CCD chip is used as an optoelectronic converter, it is necessary to link the calculation of the color components with the superimposition process of the half-lines in a suitable manner.

It goes without saying that, in this context, an optoelectronic converter C having three partial regions can also be used for converting three different signals (e.g. fluorescence signal S1, the signal of visible light S2 and fluorescence excitation signal S3).

Figure 12:
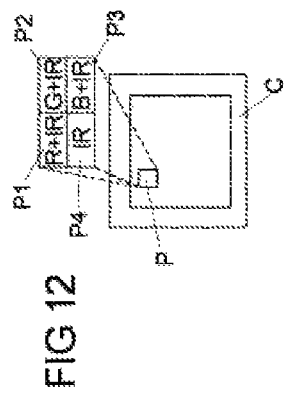
FIG. 12 shows a schematic view of a CCD chip for capturing visible light and infrared light.

FIG. 12 shows in one specific configuration the construction of an optoelectronic converter C having a number of pixel elements P which are arranged regularly in lines and columns and each consist of a group of four individual pixels P1-P4. As indicated in the schematic view, in this case three individual pixels P1-P3 serve for converting the signal of visible light by virtue of the fact that a first individual pixel P1 is sensitive to red light R, a second individual pixel P2 is sensitive to green light G and a third individual pixel P3 is sensitive to blue light B. The three individual pixels P1-P3 are additionally also sensitive to infrared light IR such that the three individual pixels P1-P3 together with a fourth individual pixel P4, which is sensitive exclusively to infrared light IR can capture and convert infrared light IR.

Figure 13:
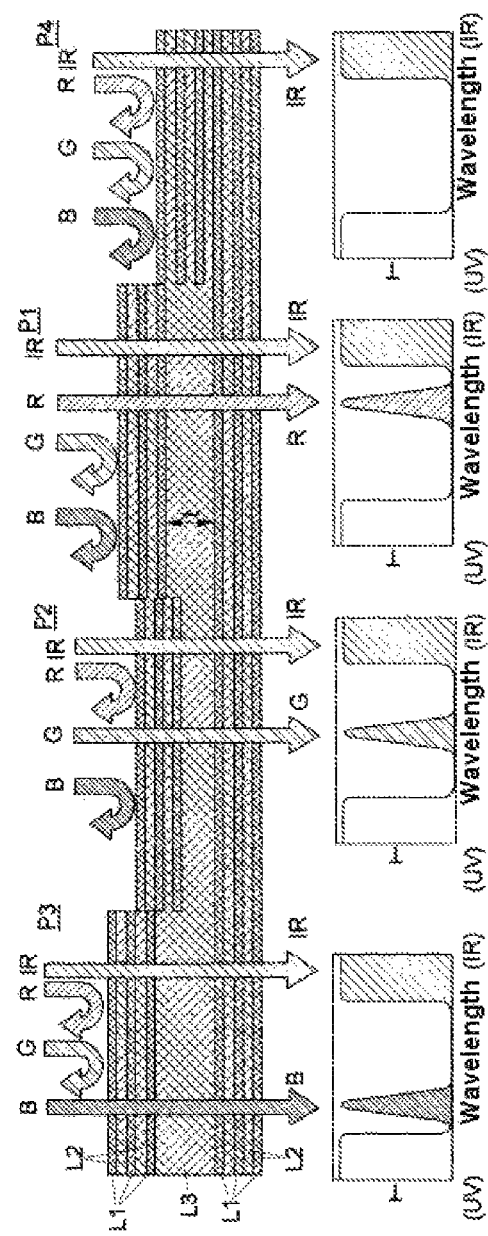
FIG. 13 shows a schematic view of a filter arrangement of the CCD chip in accordance with FIG. 12.

The configuration of the individual pixels P1-P4 for receiving red, blue or green light R, G, B and/or infrared light IR can be achieved by means of a multilayered filter arrangement such as is illustrated schematically in FIG. 13. In this case, in order to form the filter arrangement, a plurality of alternating layers L1, L2 composed of different materials are overlaid on the actual chip for receiving the light signals, a spectral transmission range being set by means of a filter layer L3 covering the entire image sensor area and having different layer thicknesses t in the region of the respective individual pixels P1-P4.

As illustrated schematically in the region of the individual pixel P4 (on the left in FIG. 13), blue light B in a predetermined frequency band is transmitted, and additionally infrared light IR as well. In the region of the individual pixel P2, by contrast, green light G and infrared light IR are transmitted and, in the region of the individual pixel P3, red light R and infrared light IR are transmitted, in order to be converted by means of the optoelectronic converter C. In the region of the individual pixel P4, finally, exclusively infrared light IR can pass through the filter arrangement, such that the individual pixel P4 is sensitive only to infrared light IR.

The associated transmission spectra are illustrated schematically below the layer arrangement and qualitatively represent the frequency ranges from ultraviolet light UV to infrared light IR in which light can pass through the layer arrangement.

Figure 9:
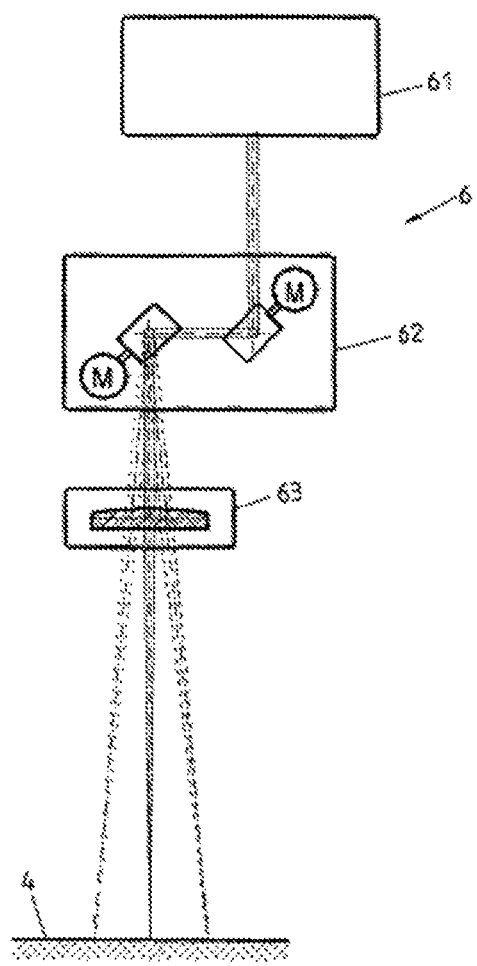
FIG. 9 shows a schematic illustration of an arrangement for projecting a fluorescence image onto an object.
Figure 10:
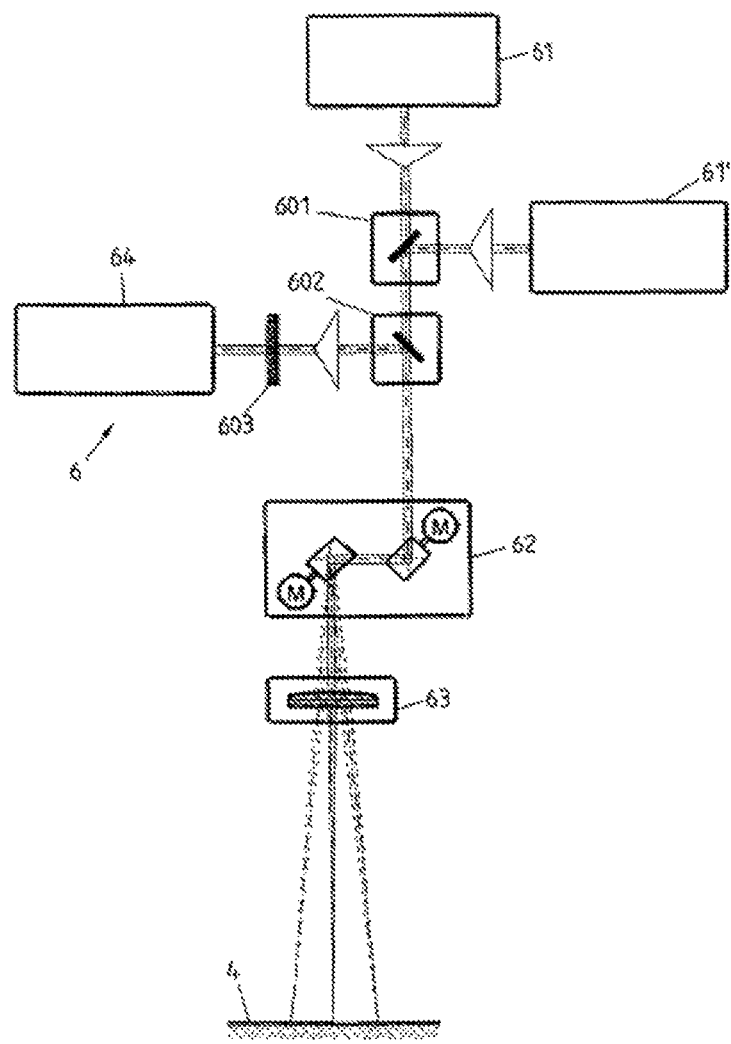
FIG. 10 shows a schematic illustration of an arrangement for capturing and for projecting a fluorescence image onto an object.
Figure 11:
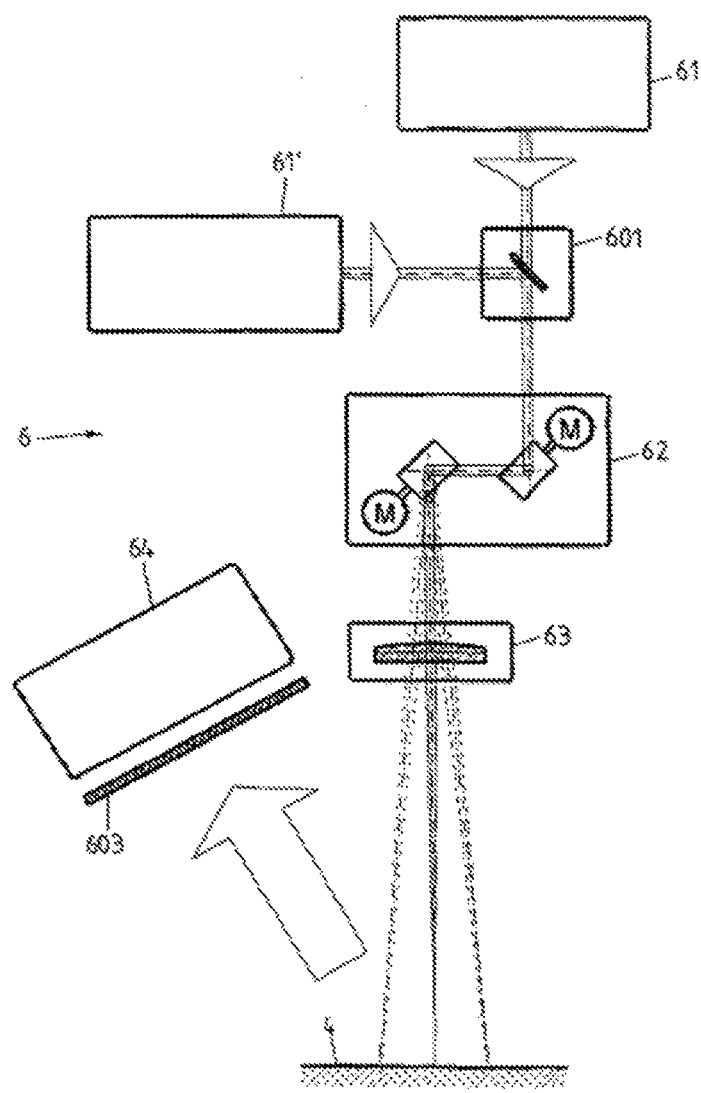
FIG. 11 shows a schematic illustration of a further arrangement for capturing and for projecting a fluorescence image onto an object.

FIGS. 9 to 11 show three different variants of devices 6 for projecting a captured fluorescence image onto the surface of an object 4. The basic concept in this case is to represent a captured fluorescence image directly on the object 4, that is to say for example on the skin surface or tissue surface of a patient and thus at the location where it arises.

Conventionally, a captured fluorescence image, output as a video output signal V, is represented on a monitor on which the fluorescence image is superimposed for example in false color on a real image. This has the consequence that an assessing physician can view the fluorescence image exclusively on the monitor, which is not a restriction in the case of an endoscopic operating technique, but can be laborious for the physician in the case of an open-surgical implementation of an operation on a patient.

In a departure from this, by means of the device 6, a captured fluorescence image can be represented in real time directly at the location at which it has been captured. Further optical aids, such as e.g. a monitor, are not necessary.

By means of the device 6, a captured fluorescence image is projected onto the object 4 with the aid of a projector or a two-axis scanner (so-called X/Y scanner). The device illustrated in FIG. 9 uses, for example an X/Y scanner 62, which, with the aid of mechanical motors and mirror arrangements projects a light beam generated by a light source 61 (for example a laser) onto the object 4 via a lens 63, by virtue of the fact that, by means of the X/Y scanner 62, an intensity modulated beam from the light source 61 (with visible light) is moved periodically over the examination region of the object 4, such that an indicator image corresponding to the fluorescence image arises there.

The modulation function of the laser beam power can rise monotonically, for example, with the local fluorescence signal. Alternatively, the characteristic of the modulation function can also be embodied as two-valued (0/1 using a threshold value), linearly proportional or logarithmically proportional.

In addition, the exact positioning of the fluorescence image on the object 4, which can be disturbed on account of the usually uneven surface of the object 4, can be improved e.g. by feedback and/or differences in the local reflectivity that possibly corrupt the indicator image can be detected and corrected in the modulation function.

An embodiment of a device 6 in which not only is a fluorescence image imaged on the object 4 but at the same time a signal is also captured from the region of the object 4 is illustrated in FIG. 10. In this case, structural parts having the same function are provided with the same reference symbols as previously.

The device in accordance with FIG. 10 serves firstly for projecting and representing the captured fluorescence image, but secondly also for capture and for this purpose can be disposed upstream of the camera head 30 of the capturing unit 3 of the imaging system 1 in accordance with FIG. 1 or FIG. 4.

In the embodiment in accordance with FIG. 10, a light source 61' generates a fluorescence excitation radiation in a wavelength range of between 700 nm and 800 nm, for example, which is radiated onto the object 4 via a beam combiner 601, a beam splitter 602, an X/Y scanner 62 and a lens 63 for the excitation of a fluorescence signal. For this purpose, by means of the X/Y scanner 62, the beam is guided over the object 4 and the object 4 is thus excited pixel by pixel.

Synchronously, the reflected fluorescence signal is guided via the lens 63 and the X/Y scanner 62 and also the beam splitter 602 and a filter 603 toward a detector 64. Capture likewise takes place pixel by pixel, the fluorescence signal from the pixel currently excited by the light source 61' being acquired.

The fluorescence signal thus received is converted and emitted in real time by means of the light source 61 as a false color signal for generating the indicator image or the relevant pixel of the indicator image on the object 4. In this case, the beam generated by the light source 61 is combined with the beam of the light source 61' by means of the beam combiner 601 and likewise directed via the X/Y scanner 62 and the lens 63 onto the object 4. In this way, a visible indication of the local fluorescence signal is represented on the object 4 directly at the location of capture in real time. As a result of the rapid scanning movement, the observer sees on the tissue surface directly an indicator image corresponding to the fluorescence image in false color.

The following advantages are afforded in the case of the embodiment in accordance with FIG. 10:

there is no image evaluation section, but rather only an individual signal processing channel;

buffer-storage of image data is not necessary;

separation of a fluorescence excitation signal relative to a signal of visible light is not necessary since a real image arises only in the observer's eye, which is not sensitive to the fluorescence excitation radiation;

in one preferred embodiment, the detector 64 can be constructed in a large-area manner and does not have to perform a movement, since the location information is predetermined by the current position of the X/Y scanner 62;

an optically simple construction having high sensitivity in the fluorescence channel results, since the detector area of the detector 64 can be chosen to be large;

simple PIN diodes with an attached filter against undesired beam components can be used as detectors;

X/Y scanners are available in a cost-effective manner;

as a marking laser it is possible to use a green laser, for example, which are likewise available in a cost-effective manner.

In another configuration, illustrated in FIG. 11, a resulting fluorescence signal can also be received by means of a detector 64 in the form of an areal CCD chip. As described above with reference to FIG. 10, in this case the object 4 is excited by means of a light source 61' by virtue of the fact that an emitted beam is guided over the object 4 by means of the X/Y scanner 62. As a result, the object 4 is progressively excited, thus giving rise to an areal excitation, from the region of which the detector 64 captures the fluorescence signal. The fluorescence image thus captured can once again be projected onto the object 4 by means of the light source 61 and via the beam combiner 601 and also the X/Y scanner 62.

The device 6 in accordance with the embodiments in FIGS. 9 to 11 can advantageously be embodied as a compact, handheld device and with modern rechargeable batteries can also be operated without cables.

The embodiments of a device for projection as illustrated in FIGS. 9 to 11 can, in principle, also be used independently of the imaging systems described in FIGS. 1 to 5 and can therefore also be regarded as independent inventions.

The invention claimed is:

1. An imaging system for the fluorescence-optical visualization of a two-dimensional or three-dimensional object, comprising:

an illumination unit, which is designed and provided for emitting optical radiation in a predetermined wavelength range in order to illuminate the object and excite a fluorescent substance contained in the object, a capturing unit, which is designed and provided for capturing an optical signal from the region of the object and for splitting the optical signal into a fluorescence signal having a first wavelength range and a signal of visible light having a second wavelength range, wherein the optical capturing unit has an optoelectronic converter having a plurality of partial regions and serving for converting the fluorescence signal into a first electronic data signal and the signal of visible light into a second electronic data signal, wherein the optical capturing unit comprises a dichroic prism for splitting the captured optical signal into the fluorescence signal and the signal of visible light, wherein the optoelectronic converter having said plurality of partial regions is arranged on an area of the dichroic prism and is connected to said area of the dichroic prism such that the optoelectronic converter with said plurality of partial regions faces the area of the dichroic prism.

2. The imaging system as claimed in claim 1, wherein of the partial regions of the optoelectronic converter a first partial region converts the fluorescence signal into a first electronic data signal and a second partial region converts the signal of visible light into a second electronic data signal.

3. The imaging system as claimed in claim 1, wherein the optical capturing unit has a dichroic prism for splitting the captured optical signal into the fluorescence signal and the signal of visible light, the dichroic prism being connected to the optoelectronic converter having a plurality of partial regions.

4. The imaging system as claimed in claim 1, wherein the captured optical signal is additionally split into a fluorescence excitation signal having a third wavelength range, which differs from the first wavelength range and the second wavelength range.

5. The imaging system as claimed in claim 4, wherein the fluorescence excitation signal has a wavelength range of between 700 nm and 800 nm.

6. The imaging system as claimed in claim 3, wherein the dichroic prism is connected to an absorber element, which absorbs a fluorescence excitation signal.

7. The imaging system as claimed in claim 3, wherein the dichroic prism is connected to a further optoelectronic converter, which converts a fluorescence excitation signal into a third electronic data signal.

8. The imaging system as claimed in claim 7, wherein the further optoelectronic converter is designed as a black-and-white converter.

9. The imaging system as claimed in claim 4, wherein the optoelectronic converter having a plurality of partial regions has a third partial region which converts the fluorescence excitation signal into a third electronic data signal.

10. The imaging system as claimed in claim 4, wherein a partial region of the optoelectronic converter having a plurality of partial regions converts both the signal of visible light and the fluorescence excitation signal.

11. The imaging system as claimed in claim 1, wherein the illumination unit has an optical coupling element for coupling the fluorescence excitation radiation and the radiation in the range of visible light and couples the coupled optical radiation thus generated into an optical waveguide for illuminating the object.

12. The imaging system as claimed in claim 11, wherein the optical waveguide can be connected to an element for adapting the emission characteristic of the optical radiation for illuminating the object from outside or for illuminating regions within the object.

13. The imaging system as claimed in claim 12, wherein the optical waveguide, for adapting the emission characteristic, can be connected to at least one of a diffuser or an endoscope.

14. The imaging system as claimed in claim 1, wherein the imaging system has a control and processing unit for controlling at least one of the illumination unit or the capturing unit.

15. The imaging system as claimed in claim 14, wherein the control and processing unit is designed to generate from the acquired signals a real image obtained from at least one of the signal of visible light, a fluorescence image obtained from the fluorescence signal or an infrared absorption image obtained from a fluorescence excitation signal.

16. The imaging system as claimed in claim 15, wherein at least one of the fluorescence image or the infrared absorption image are super-imposed on the real image or the individual images are displayed alongside one another.

17. The imaging system as claimed in claim 1, further comprising a two-axis scanner for projecting a generated fluorescence image onto the object.

18. The imaging system as claimed in claim 17, wherein the two-axis scanner is designed to direct a light beam of a light source for generating a fluorescence image on the object periodically over the object.

19. The imaging system as claimed in claim 17, wherein the two-axis scanner is additionally designed to at least one of direct optical radiation of a light source onto the object or to direct optical signals from the object toward a detector.

20. A method for the fluorescence-optical visualization of a two-dimensional or three-dimensional object, in which:
- an optical radiation is emitted in a predetermined wavelength range in order to illuminate the object and excite a fluorescent substance contained in the object,
- an optical signal is captured from the region of the object and the optical signal is split into a fluorescence signal having a first wavelength range and a signal of visible light having a second wavelength range,
- wherein a dichroic prism splits the captured optical signal into the fluorescence signal and the signal of visible light and an optoelectronic converter connected to the dichroic prism and having a plurality of partial regions converts the fluorescence signal in a first electronic data signal by means of a first partial region and converts the signal of visible light into a second electronic data signal by means of a second partial region,
- wherein the optical capturing unit comprises a dichroic prism which splits the captured optical signal into the fluorescence signal and the signal of visible light,
- wherein the optoelectronic converter having said plurality of partial regions is arranged on an area of the dichroic prism and is connected to said area of the dichroic prism such that the optoelectronic converter with said plurality of partial regions faces the area of the dichroic prism.

* * * * *